United States Patent
Bowald et al.

[11] Patent Number: 5,431,683
[45] Date of Patent: Jul. 11, 1995

[54] ELECTRODE SYSTEM FOR A DEFIBRILLATOR

[75] Inventors: Staffan Bowald, Almunge; Jens Wolf, Johaneshov; Jakub Hirschberg, Taeby, all of Sweden

[73] Assignee: Pacesetter AB, Solna, Sweden

[21] Appl. No.: 161,410

[22] Filed: Dec. 6, 1993

[30] Foreign Application Priority Data

Dec. 11, 1992 [SE] Sweden ................ 9203735

[51] Int. Cl.⁶ .............................................. A61N 1/39
[52] U.S. Cl. ....................................... 607/5; 607/119; 607/122
[58] Field of Search ................. 607/4–9, 607/123, 116, 119, 122, 129, 130, 131, 148; 128/642

[56] References Cited

U.S. PATENT DOCUMENTS

| | | | |
|---|---|---|---|
| 3,942,536 | 3/1976 | Mirowski et al. | 128/419 |
| 4,708,145 | 11/1987 | Tacker, Jr. et al. | 128/419 |
| 4,727,877 | 3/1988 | Kallok | 128/419 |
| 5,044,375 | 9/1991 | Bach, Jr. et al. | 128/786 |
| 5,099,838 | 3/1992 | Bardy | 128/419 |
| 5,163,427 | 11/1992 | Keimel | 128/419 |
| 5,165,403 | 11/1992 | Mehra | 128/419 |
| 5,269,326 | 12/1993 | Verrier | 128/642 |
| 5,380,404 | 9/1994 | Adams et al. | 607/5 |

FOREIGN PATENT DOCUMENTS

| | | |
|---|---|---|
| 0373953 | 6/1990 | European Pat. Off. . |
| WO92/11896 | 7/1992 | WIPO . |
| WO92/18198 | 10/1992 | WIPO . |

Primary Examiner—William E. Kamm
Assistant Examiner—Marianne Parker
Attorney, Agent, or Firm—Hill, Steadman & Simpson

[57] ABSTRACT

An implantable cardioverter/defibrillator has an electrode system including two electrodes, at least one of the two electrodes being adapted for placement in a peripheral vein of the heart, the peripheral veins constituting the venous side of the coronary vessels running between the base of the heart and the apex of the heart.

32 Claims, 4 Drawing Sheets

ELECTRODE SYSTEM FOR A DEFIBRILLATOR

BACKGROUND OF THE INVENTION

1. Field of the Invention

The present invention is directed to an electrode system intended for proximal connection to a cardioverter/defibrillator, and for distal placement in the region of the heart in order to deliver electrical energy to the heart from the cardioverter/defibrillator to terminate an arrhythmia in the heart, and in particular to such an electrode system having at least two electrodes.

2. Description of the Prior Art

In defibrillation/cardioversion (cardioversion in this context meaning a lower energy defibrillation; the generic designation ("defibrillation" will be used hereinafter) using, for example, a three-electrode system with two intravascular electrodes, one of these intravascular electrodes is normally placed in the right ventricle, and another either in the superior vena cava or, less commonly, in the inferior vena cava. It is also known to place one of the electrodes in the coronary sinus and its tributary along the base of the heart (i.e., the portion of the great cardiac vein which runs along the base of the heart). In order to achieve a highly efficient utilization of the energy stored in the defibrillator, as well as to achieve good distribution of current in the heart while simultaneously avoiding the need for major surgery (thoracostomy), the third electrode is devised as a subcutaneous, large-area electrode, i.e., a patch electrode. The patch electrode is usually placed in the vicinity of the left ventricle, between the patient's ribs and skin.

An electrode systems with the above-described vascular placement is disclosed in U.S. Pat. No. 4,708,145. This patent discloses intravascular electrodes carried on a common electrode cable for a plurality of electrodes in the right ventricle and the superior vena cava. It is also known to provide separate electrode cables for different electrodes, and a separate sensor electrode for a sensor for detecting cardiac events. Such versions of electrode systems are disclosed in U.S. Pat. No. 4,727,877, European Application 0 373 953 and U.S. Pat. No. 5,044,375.

The use of systems with only two (non-epicardiac) electrodes is also known. An example of such a system is disclosed in U.S. Pat. No. 3,942,536, in which the electrodes, carried on a common electrode cable, are placed in the superior vena cava and the right ventricle, respectively.

In those systems which make use of the coronary vessels on the venous side of the heart as a site for at least one of the defibrillation electrodes, the coronary vessels which have been employed for this purpose are the coronary sinus and its tributary (a portion of great cardiac vein) running along the base of the heart, i.e, along the valve plane of the heart.

SUMMARY OF THE INVENTION

It is an object of the present invention to provide an electrode system for a defibrillator which achieves a highly efficient utilization of the energy stored in the defibrillator while providing a favorable distribution of current in the heart, which constitutes an improvement over known systems.

The above object is achieved in accordance with the principles of the present invention in a defibrillator apparatus, and a method for defibrillating a heart, wherein at least one electrode is sited in a peripheral vein. As used herein, "peripheral veins" encompasses the venous side of the coronary vessels running between the base and the apex of the heart. The include the middle and small cardiac veins, and the portion of the great cardiac vein which runs between the base and apex of the heart. The definition of "peripheral veins" used herein, therefore, excludes that portion of the great cardiac vein which runs along the base plane of the heart, which has been used a site for electrode placement in prior art electrode systems.

The electrode placed in a peripheral vein in accordance with the principles of the present invention interacts with the other electrodes in the system, and has been shown to produce a highly efficient utilization of the energy stored in the defibrillator, together with a favorable distribution of current in the heart. In view of the aforementioned prior art electrode systems, the favorable effect of this placement is surprising because, for example, the aforementioned European Application 0 373 953 emphasizes the importance of restricting electrode placement only to those coronary vessels running along the base of the heart (see col. 6, lines 24–33 of European Application 0 373 953).

In various embodiments of the invention, at least some of the venous electrodes can be arranged on a common electrode cable, and/or can be provided with means for affixing the electrodes to the inner venous wall. The fixing means can be in the form of a hollow, resilient cylinder, which achieves fixing by radial expansion. The hollow cylindrical shape of the electrode enables blood to flow unimpeded through the electrode.

DESCRIPTION OF THE PREFERRED EMBODIMENTS

Identical reference designations are used to identify identical or similar components in all the figures.

Figure 1:
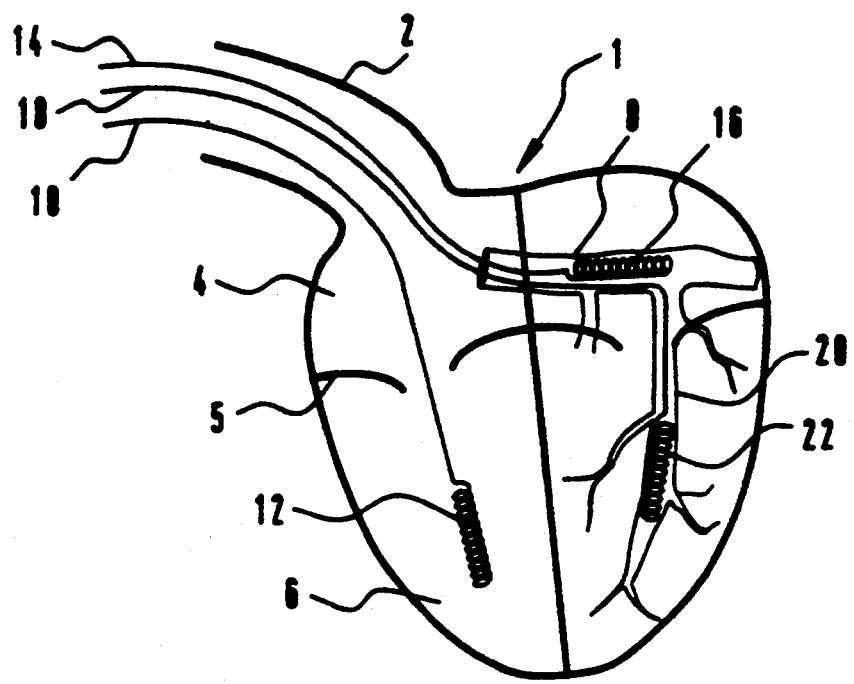
FIG. 1 is a schematic representation of a human heart in cross section (frontal plane) showing an electrode system connected in the heart constructed in accordance with the a first embodiment of the present invention and operating in accordance with the method of the invention.

FIG. 1 shows a cross-section of a human heart 1 and a number of blood vessels which are important to the invention. A first electrode cable 10, introduced via the superior vena cava 2, passes through the right atrium 4 and the valve plane 5 and exits into the right ventricle 6. At or near its distal end, the cable 10 is provided with an electrode 12 which can be anchored in the right ventricle. A second electrode cable 14, also introduced via the superior vena cava 2, passes through the right atrium 4 but, in contrast to the cable 10, does so in a manner so that the cable 14 exits into the coronary sinus 8 and its tributary (continuation) along the base of the heart 1. The cable 14 has a distal end provided with an electrode 16 which can be anchored in the coronary sinus or its tributary. A third electrode cable 18, also introduced via the superior vena cava 2, passes through the right atrium 4 and the coronary sinus 8, and possibly through its tributary, so that the cable 18 exits into a peripheral vein 20 of the heart 1, as shown in FIG. 1. The cable 18 has a distal end at which an electrode 22 is disposed, which can be anchored in the peripheral vein 20. The electrodes 12, 16 and 22 are connectable to an implantable defibrillator (not shown) via conductors in the respective cables 10, 14 and 18.

Figure 2:
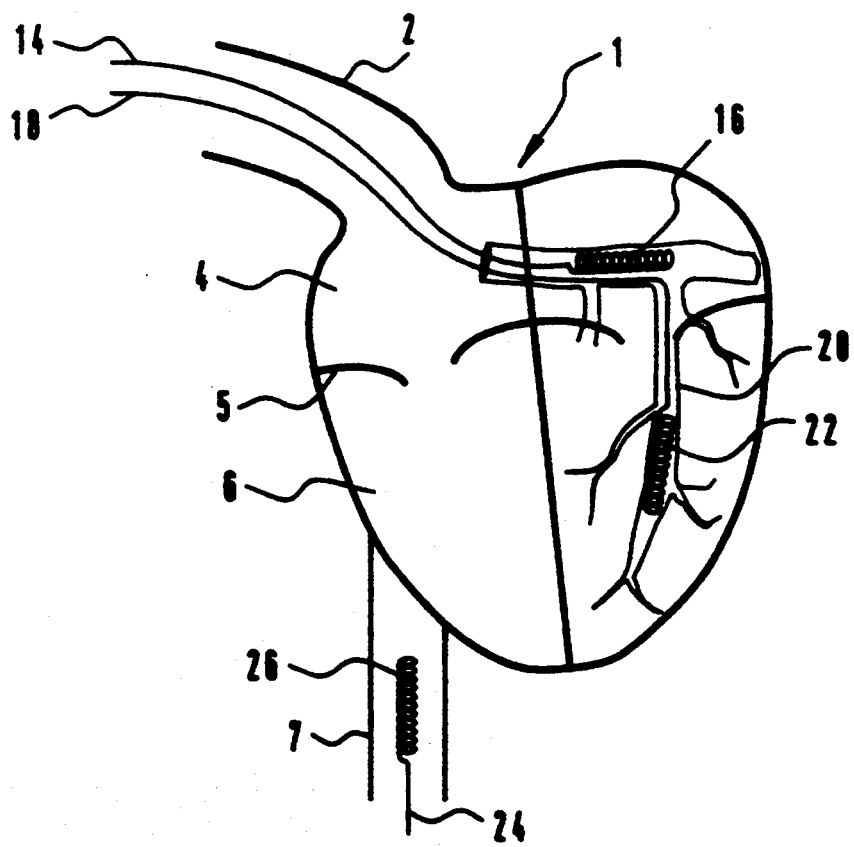
FIGS. 2–8 also show a human heart in cross section (frontal plane) and respectively show further embodiments of the electrode system constructed in accordance with the principles of the present invention, arranged in the heart.

The electrode system shown in FIG. 2 differs from the system shown in FIG. 1 in that the electrode 12 placed in the right ventricle 6 in the embodiment of FIG. 1, is replaced by an electrode 26, placed in the inferior vena cava 7, in the embodiment of FIG. 2. The electrode 26 is connectable to the implantable defibrillator via a conductor in the electrode cable 24.

Figure 3:
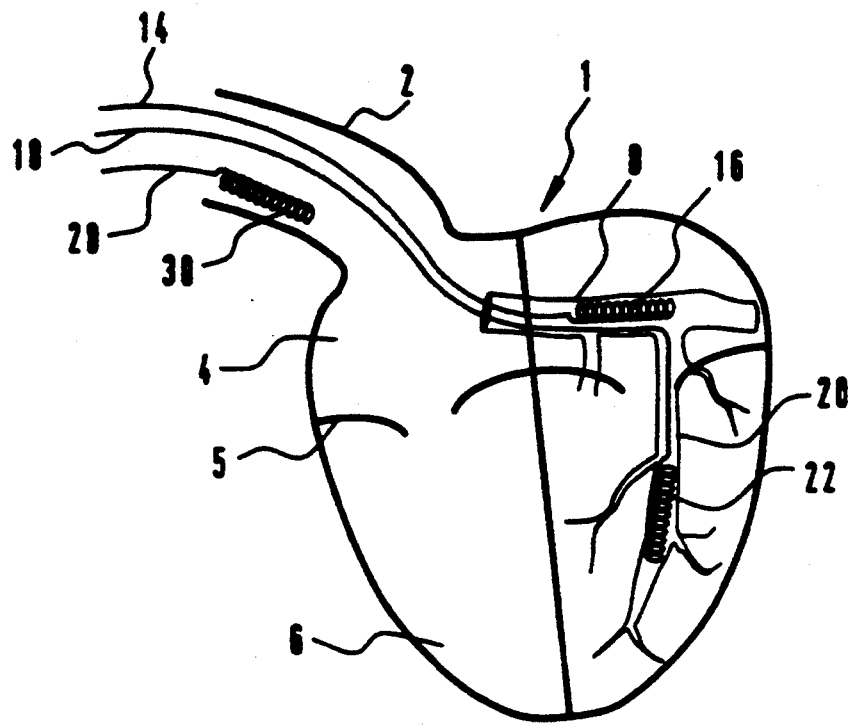
Figure 4:
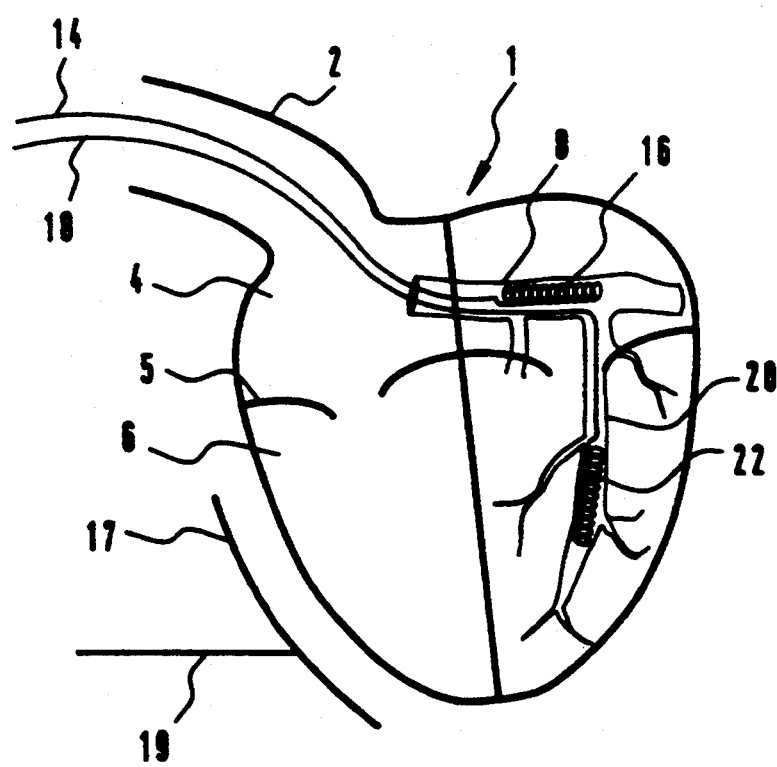
Figure 5:
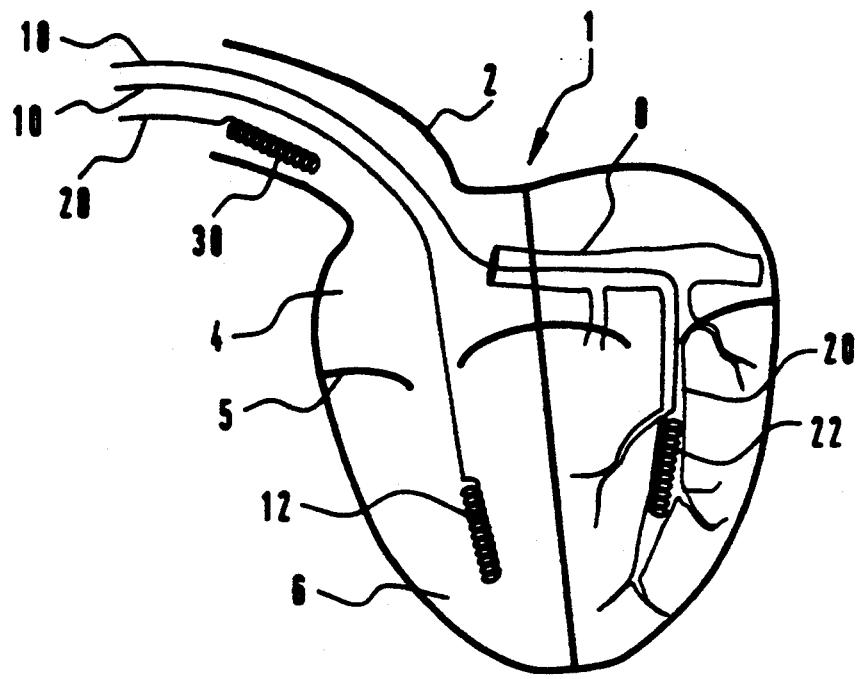
Figure 6:
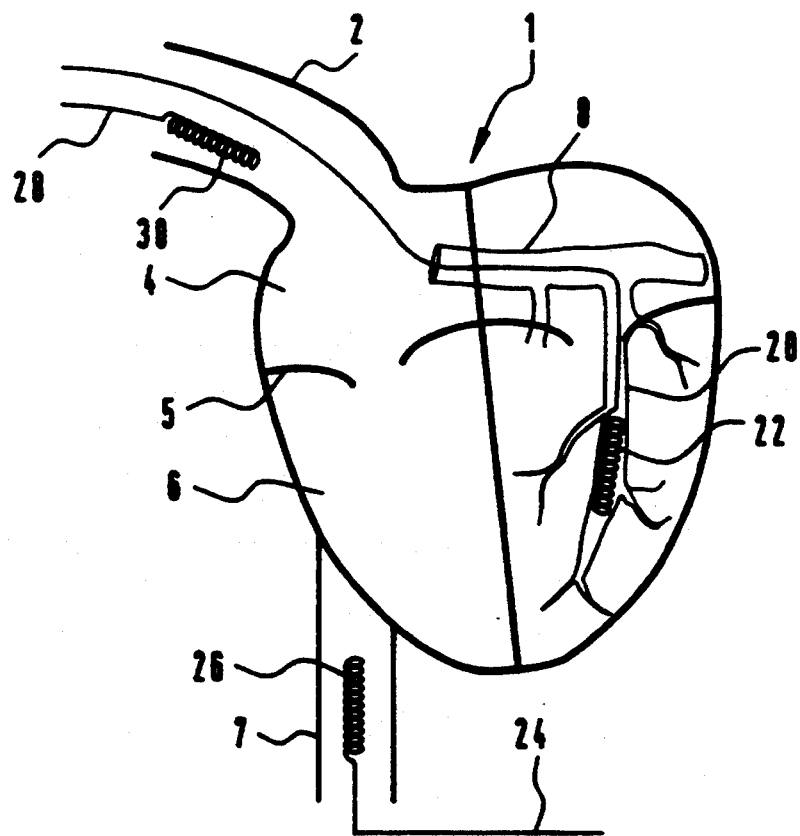
Figure 7:
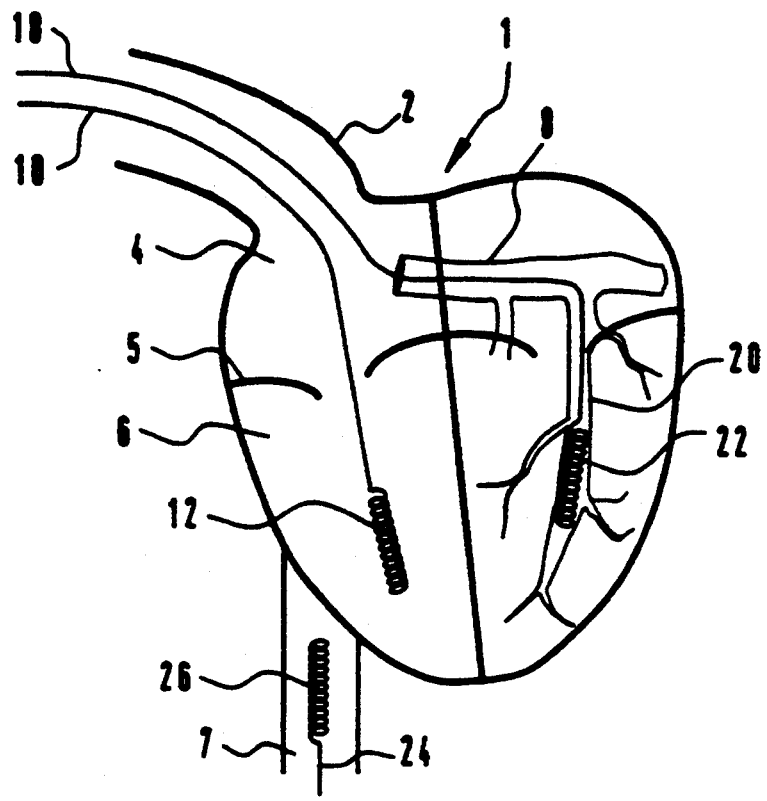
Figure 8:
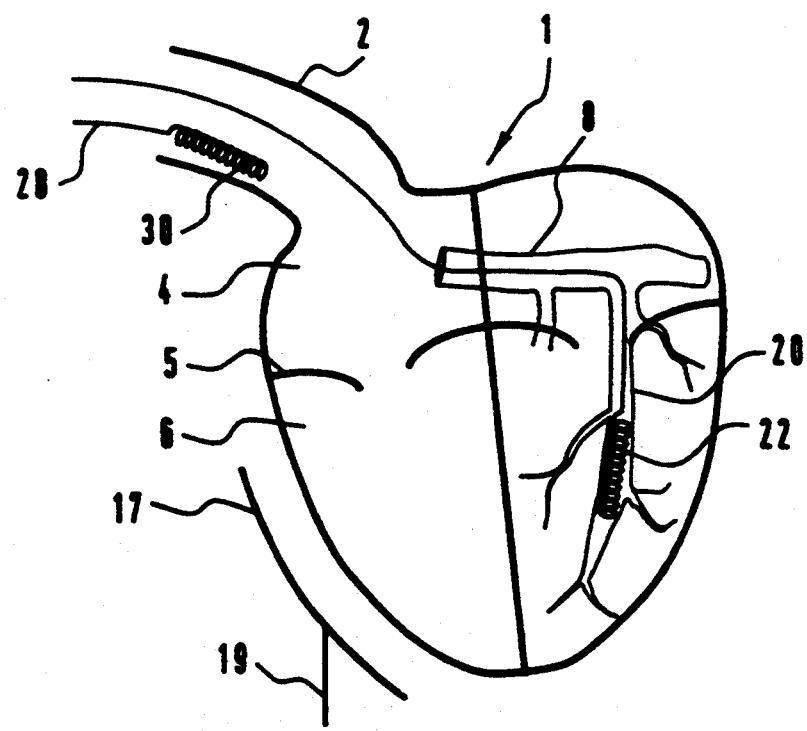

In the electrode system shown in FIG. 3, the electrode 12 in the right ventricle 6 in the system of FIG. 1 is replaced by the electrode 30 placed in the superior vena cava 2. In the embodiment of FIG. 4, the right ventricle electrode 12 in the system of FIG. 1 has been replaced with a subcutaneous patch electrode 17, placed near the right ventricle 6. The electrodes 30 and 17 in the embodiments of FIGS. 3 and 4 are connectable to the implantable defibrillator via conductors in the respective electrode cables 28 and 19. As used herein, subcutaneous placement means placement between the ribs and skin. Alternatively, the enclosure (housing) of the defibrillator can be used as a patch electrode.

The electrode systems shown in FIGS. 5, 6, 7 and 8 respectively show further configurations of the above-described electrode components. The electrode system shown in FIGS. 5, 6 and 8 have in common the use of an electrode 30 in the superior vena cava 2 instead of the electrode 16 in the coronary sinus 8 in the systems shown in FIGS. 1, 2 and 4. The system shown in FIG. 7 employs an electrode configuration including the electrode 12 in the right ventricle 6, the electrode 22 in a peripheral vein 20, and the electrode 26 in the inferior vena cava 7.

It should be noted that the peripheral vein 20 which is used in the various systems as an electrode site is for exemplary purposes only, and any peripheral vein falling within the above-identified definition of "peripheral veins" can serve as a site for that electrode. The choice of the particular peripheral vein which used will be governed to a large extent by the selected placement of the other electrodes.

Connection of the electrodes shown in the different embodiments of FIGS. 1 through 8 to the implanted defibrillator, and to each other, can be achieved in various ways. For example, the electrodes 16 and 22 shown in FIG. 1 can be interconnected so that the defibrillation pulse is present between (across) these electrodes, and is also across each of these electrodes and the electrode 12 in the right ventricle 6.

Alternatively, the electrodes 12, 16 and 22 can be interconnected so the defibrillation pulse is present across any one of these electrodes and the other two of the electrodes. Alternately, each of the electrodes 12, 16 and 22 can be set at respectively different voltage during defibrillation, or as an additional alternative can emit defibrillation pulses sequentially in pairs. Monophasic, biphasic or multiphasic defibrillation pulses can be used.

The cables 14 and 18 for the respective electrodes 16 and 22 shown in FIG. 1 can be replaced with a common electrode cable for both electrodes 16 and 22. The inferior vena cava 7 can be used as an alternative to the described routing of the intravascular electrodes through the superior vena cava 2. The intravascular electrodes introduced via the former route can also share an electrode cable, or may have separate electrode cables. In the configuration shown in FIG. 3, the electrodes 16, 22 and 30 can have a single, common catheter.

All configurations, with the exception of those making use of the subcutaneous patch electrode 17, using the same implantation route for a plurality of electrodes, can have all electrodes arranged on a common electrode cable.

The aforementioned electrode configurations can also be supplemented with a separate sensor electrode for detecting cardiac events and/or a sensor for sensing different physiological parameters related to, for example, cardiac hemodynamics. The electrode cable of the sensor electrode can also include a stimulation electrode for a pacing function.

The intravascular electrodes 16, 22, 26 and 30 are maintained in place in their respective veins by a structure making those electrodes radially expandable, so that in their expanded position these electrodes assume at least the contours of a hollow cylinder. Defibrillation electrodes having such a structure are described in detail in Applicants' co-pending application entitled "Defibrillation Electrode" (Attorney's Docket No. P93,294), the teachings of which are incorporated herein by reference. Thus, the intravascular electrodes 16, 22, 26 and 30 are maintained in place in the respective vein by being formed as helices having a bias force operating in a direction transversely to the longitudinal axis of the helix, which exerts pressure on the venous wall. To avoid repetition, only helical fixing of the electrode 26 in the inferior vena cava 7 will be described below, but the description applies equally to the other intravascular electrodes.

In its pre-shaped state, the helical electrode 26 can be considered as being helically wound around an imaginary cylinder having an external diameter which is somewhat larger than the inner diameter of the inferior vena cava 7. The helix can consist of an electrically conductive, biocompatible material. The electrode 26 is connected to the electrode cable 24 so as to form a continuous unit. A centrally located longitudinal channel, into which a stylet can be introduced, runs through the electrode 26 and the electrode cable 24. During implantation, the electrode 26 is straightened with aid of the stylet. The electrode 26, whose diameter during implantation is therefore smaller than the diameter of the blood vessels it is to traverse, can then be introduced into the inferior vena cava 7. When the implanting physician decides that the electrode 26 has reached an appropriate site in the inferior vena cava 7, the stylet is withdrawn, and the electrode 26 reassumes its pre-shaped, helical configuration. The pressure of the helix against the venous wall keeps the helix at the desired site. In the affixed position, the electrode 36 forms a relatively large electrode surface against the vascular wall. The electrode 26 also has the advantage of allowing blood in the vessel to flow unimpeded through the interior of the helix. The risk of clot formation is thereby minimized. Additionally, the electrode 26 can easily be re-positioned if the stylet is re-inserted into the central channel and is again used to straighten the electrode 26. The implanting physician can thus readily find a site for the electrode 26 which, in combination with the sites of other electrodes, provides favorable distribution of current in the heart tissue.

For implantation, the physician can use an introductory catheter instead of a stylet. The electrode cable 24, with the straightened electrode 26, is inserted in the introductory catheter, the catheter being sufficiently stiff to maintain the electrode 26 straightened during implantation. When the electrode 26 has been advanced to the desired position in the inferior vena cava 7, the introductory catheter can be withdrawn so that the electrode 26 reassumes its pre-coiled configuration.

In instances wherein the electrodes such as the electrodes 16 and 22, are arranged on a common electrode cable, implantation can be performed using a single stylet running through a central channel in all the electrodes and through the electrode cable. Both electrodes are then straightened during implantation. When the electrode 22 reaches a desired position, the stylet is withdrawn just enough to allow the electrode 22 to reassume its helical configuration, the electrode 16 thereafter being positioned at a desired site in the coronary sinus 8. When the electrode 16 has been properly positioned, the stylet is completely withdrawn so that the electrode 16 reassumes its pre-shaped configuration. An introductory catheter can alternatively be used instead of a stylet.

The electrode 16 intended for placement in the coronary sinus 8 and its tributary along the base of the heart can be formed, for example, by two sub-electrodes respectively disposed in the coronary sinus 8 and its tributary. The two sub-electrodes can be arranged on a common continuation of the electrode cable 14. The two sub-electrodes respectively placed in the coronary sinus 8 and its tributary can be individually adapted to achieve additionally improved distribution of the current in the heart. Implantation is undertaken in the above-described way. It is also possible to use more than two such sub-electrodes. The electrode 22 placeable in a peripheral vein 20 can also be composed of two or more sub-electrodes.

Although modifications and changes may be suggested by those skilled in the art, it is the intention of the inventors to embody within the patent warranted hereon all changes and modifications as reasonably and properly come within the scope of their contribution to the art.

We claim as our invention:

1. An electrode system for a defibrillator comprising: a plurality of electrode means, a first of said plurality of electrode means comprising intravenously placeable means for delivering energy from a site located in a peripheral vein of a heart for defibrillating said heart.

2. An electrode system as claimed in claim 1 wherein a second of said plurality of electrode means comprises intravenously placeable means for delivering energy from a site located in the coronary sinus and its tributary along the base of said heart for defibrillating said heart.

3. An electrode system as claimed in claim 2, wherein said plurality of electrode means includes a third of said electrode means comprising means for interacting with said first and second of said plurality of electrode means for defibrillating said heart.

4. An electrode system as claimed in claim 3 wherein said third of said plurality of electrode means comprises endocardiac means for delivering energy from a site located in the right ventricle of said heart for defibrillating said heart.

5. An electrode system as claimed in claim 3 wherein said third of said plurality of electrode means comprises intravenously placeable means for delivering energy from a site located in the inferior vena cava for defibrillating said heart.

6. An electrode system as claimed in claim 3 wherein said third of said plurality of electrode means comprises intravenously placeable means for delivering energy from a site located in the superior vena cava for defibrillating said heart.

7. An electrode system as claimed in claim 3 wherein said third of said plurality of electrode means comprises subcutaneously placeable patch electrode means for delivering energy from a site located in a vicinity of the exterior of the right ventricle of said heart for defibrillating said heart.

8. An electrode system as claimed in claim 7 further comprising a defibrillator to which said plurality of electrode means are connected, said defibrillator having a defibrillator housing, and wherein said patch electrode comprises at least a portion of said defibrillator housing.

9. An electrode system as claimed in claim 2 further comprising an electrode cable and wherein said second of said electrode means comprises at least two sub-electrodes carried on said electrode cable.

10. An electrode system as claimed in claim 1 wherein a second of said plurality of electrode means comprises intravenously placeable means for delivering energy from a site located in the superior vena cava for defibrillating said heart.

11. An electrode system as claimed in claim 10 wherein said plurality of electrode means includes a third of said electrode means comprising means for interacting with said first and second of said plurality of electrode means for defibrillating said heart.

12. An electrode system as claimed in claim 11 wherein said third of said electrode means comprises endocardially placeable means for delivering energy from a site located in the right ventricle of said heart for defibrillating said heart.

13. An electrode system as claimed in claim 11 wherein said third of said electrode means comprises electrode means for delivering energy from a site in the inferior vena cava for defibrillating said heart.

14. An electrode system as claimed in claim 11 wherein said third of said electrode means comprises subcutaneously placeable patch electrode means for delivering energy from a site located in a vicinity of the exterior of the right ventricle of said heart for defibrillating said heart.

15. An electrode system as claimed in claim 14 further comprising a defibrillator to which said plurality of electrode means are connected, said defibrillator having a defibrillator housing, and wherein said patch electrode means comprises at least a portion of said defibrillator housing to which said electrodes in said electrode system are connected.

16. An electrode system as claimed in claim 1 wherein said plurality of electrode means includes second electrode means and third electrode means, and wherein said second electrode means comprises endocardially placeable means for delivering energy from a site located in the right ventricle of said heart for defibrillating said heart and said third electrode means comprises intravenously placeable means for delivering energy from a site located in the inferior vena cava for defibrillating said heart.

17. An electrode system as claimed in claim 1, wherein said plurality of electrode means includes a plurality of intravenously placeable means for delivering energy from respective sites each located in a different vein for defibrillating said heart, including said first of said plurality of electrode means, and further comprising a common cable carrying at least two of the intravenously placeable means.

18. An electrode system as claimed in claim 1 wherein said plurality of electrode means includes a plurality of intravenously placeable means for delivering energy from respective sites each located in a different vein for defibrillating said heart, including said first of said plurality of electrode means, and wherein each of said intravenously placeable means includes means for affixing that respective intravenously placeable means to an inner wall of the vein in which that respective intravenously placeable means is disposed.

19. An electrode system as claimed in claim 18 wherein said means for affixing comprises an electrode body having a hollow, cylindrical shape with a radius exceeding a radius of said vein for affixing said electrode body by pressure against said inner wall of said vein.

20. An electrode system as claimed in claim 19 wherein said electrode body consists of a helix having a plurality of helical turns forming a surface of a cylinder.

21. An electrode system as claimed in claim 1 further comprising an electrode cable and wherein said first of said electrode means comprises at least two separate sub-electrodes carried on said electrode cable.

22. A method for defibrillating a heart comprising the steps of:
arranging a plurality of electrodes, including a first defibrillation electrode, relative to a heart;
placing said first defibrillation electrode intravenously in a peripheral vein of said heart; and
delivering a plurality of defibrillation pulses to said heart via said plurality of electrodes.

23. A method as claimed in claim 22 wherein said plurality of electrodes includes a second electrode, and comprising the additional step of:
placing said second electrode intravenously in the coronary sinus and its tributary along the base of the heart.

24. A method as claimed in claim 23 wherein said plurality of electrodes includes a third electrode, and comprising the additional step of:
placing said third electrode in the right ventricle.

25. A method as claimed in claim 23 wherein said plurality of electrodes includes a third electrode, and comprising the additional step of:
placing said third electrode intravenously in the inferior vena cava.

26. A method as claimed in claim 23 wherein said plurality of electrodes includes a third electrode, and comprising the additional step of:
placing said third electrode intravenously in the superior vena cava.

27. A method as claimed in claim 23 wherein said plurality of electrodes includes a third electrode consisting of a patch electrode, and comprising the additional step of:
placing said third electrode subcutaneously in the vicinity of the right ventricle.

28. A method as claimed in claim 22 wherein said plurality of electrodes includes a second electrode, and comprising the additional step of:
placing said second electrode intravenously in the superior vena cava.

29. A method as claimed in claim 28 wherein said plurality of electrodes includes a third electrode, and comprising the additional step of:
placing said third electrode in the right ventricle.

30. A method as claimed in claim 28 wherein said plurality of electrodes includes a third electrode, and comprising the additional step of:
placing said third electrode intravenously in the inferior vena cava.

31. A method as claimed in claim 28 wherein said plurality of electrodes includes a third electrode consisting of a patch electrode, and comprising the additional step of:
placing said third electrode subcutaneously in the vicinity of the right ventricle.

32. A method as claimed in claim 22 wherein said plurality of electrodes includes a second electrode and a third electrode, and comprising the additional steps of:
placing said second electrode in the right ventricle; and
placing said third electrode intravenously in the inferior vena cava.

* * * * *